(12) United States Patent
Cameron et al.

(10) Patent No.: US 8,575,563 B2
(45) Date of Patent: Nov. 5, 2013

(54) COMPACT ISOCENTRIC GANTRY

(75) Inventors: John M. Cameron, Bloomington, IN (US); Vladimir Anferov, Bloomington, IN (US); Timothy A. Antaya, Hampton Falls, NH (US)

(73) Assignee: ProCure Treatment Centers, Inc., New York, NY (US)

( * ) Notice: Subject to any disclaimer, the term of this patent is extended or adjusted under 35 U.S.C. 154(b) by 114 days.

(21) Appl. No.: 12/917,927

(22) Filed: Nov. 2, 2010

(65) Prior Publication Data

US 2011/0101236 A1    May 5, 2011

Related U.S. Application Data

(60) Provisional application No. 61/257,329, filed on Nov. 2, 2009.

(51) Int. Cl.
*H05H 13/00* (2006.01)

(52) U.S. Cl.
USPC ....... 250/396 R; 250/397; 250/398; 250/400; 250/396 ML; 315/500; 315/501; 315/502

(58) Field of Classification Search
USPC ............... 250/492.1, 492.3, 396 R, 398, 400, 250/396 ML; 315/500, 501, 502, 503, 504, 315/505, 506, 507
See application file for complete search history.

(56) References Cited

U.S. PATENT DOCUMENTS

| | | | |
|---|---|---|---|
| 3,866,251 A | 2/1975 | Pounds | |
| 4,531,813 A | 7/1985 | Van Den Berg | |
| 5,375,276 A | 12/1994 | Nelson et al. | |
| 5,787,879 A | 8/1998 | Gibson | |
| 6,683,318 B1 * | 1/2004 | Haberer et al. | 250/492.3 |

FOREIGN PATENT DOCUMENTS

WO    WO2008/081480 A1    7/2008

* cited by examiner

*Primary Examiner* — Robert Kim
*Assistant Examiner* — Hanway Chang
(74) *Attorney, Agent, or Firm* — Shay Glenn LLP

(57) ABSTRACT

A gantry for administering proton beam therapy with improvements which reduce the size, weight, costs and radiation beam loss associated with proton beam therapy systems currently commercially available. The gantry utilizes achromatic superconducting multi-function electromagnet systems wherein the magnets can include dipoles and quadrupoles. The achromatic properties of the rampable magnet systems allow for ease of transmission of the beam whose energy is rapidly changed through a large range of different energies without changing of the strength of the magnetic fields or dipole settings. The magnets may be made with either low or high temperature superconductors. The gantry design further integrates beam scanning but keeps the gantry isocentric. A much greater fraction of the beam can be transmitted through the gantry than with current art, thereby reducing radiation shielding requirements and the demand put on the accelerator to produce large quantities of proton beam.

26 Claims, 10 Drawing Sheets

COMPACT ISOCENTRIC GANTRY

CROSS REFERENCE TO RELATED APPLICATIONS

This application claims the benefit under 35 U.S.C. 119 of U.S. Provisional Patent Application No. 61/257,329, filed Nov. 2, 2009, titled "Compact Isocentric Gantry". This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention generally relates to proton therapy. More specifically, the present invention relates to compact isocentric gantries for use in proton therapy centers.

BACKGROUND OF THE INVENTION

Over half of all patients in the US with cancer are treated with radiation therapy.

Radiation therapy is based on irradiating the patient, more particularly his or her tumor, with ionizing radiation. In the particular case of proton radiation therapy, the radiation is performed using a proton beam. It is the dose of radiation delivered to the tumor which is responsible for its destruction. Proton therapy is a desired form of radiation therapy because, in comparison to standard x-ray radiation therapy, proton therapy allows an increased dose of radiation to a tumor while reducing the amount of radiation to the healthy tissue surrounding it.

The central challenge to modern radiation therapy is to enhance local tumor control using dose escalation and to minimize the dose to normal tissues in order to improve survival and the quality of life of the patients. Radiation can damage normal tissue and thus causes both short term and later stage tumors in long-term cancer survivors.

The recent progress made by 3D conformal and intensity-modulated radiation therapy has reduced short term radiation-induced complications especially in dose-limiting organs like the brain, lung and intestine. Yet, acute short term complications do occur and are still the limiting factor for some treatments. More insidious for younger patients is the long term potential occurrence of secondary tumors for years and even decades after the treatment.

The replacement of x-ray therapy with protons will have substantial long term benefit to patients due to greatly reduced long and short term toxicity side effects. Such effects also have substantial costs associated with their treatment that may continue for many years after treatment. If the cost of proton therapy can be made about equivalent to that of x-rays for the primary treatment, they would result in substantial long term savings to health care providers.

One of the major roadblocks to the greater application of proton therapy is that of cost. The capital cost of a proton therapy center is due both to the cost of the very large equipment and of the heavily shielded vaults in which it is installed. However, the technology now included in FDA approved proton systems dates from some 20 years ago. It does not reflect advances made by researchers in the technology for use in research laboratories, in particular the use of high temperature superconductors.

A conventional proton therapy facility is typically composed of the particle accelerator, the proton beam guiding and controlling device, and the treatment rooms. The particle accelerator actually is not the dominating component in the layout of a conventional proton therapy facility where the accelerated beam is shared by several treatment rooms. When one takes a bird's eye view of a traditional four room facility, it is evident that the largest component of the overall proton beam delivery system is the proton beam guiding and controlling device, hereafter referred to as the gantry. The gantry transports and delivers the proton beam into a treatment room, bends the beam until it can be incident orthogonal to the patient and then rotates the beam around the patient. A typical gantry is comprised of large magnets, an evacuated pipe, a nozzle and a counterweight. All of the components are mounted on a large steel beam "squirrel cage" to enable the rotation of the proton beam around the patient.

FIG. 1 is one embodiment of a conventional treatment room floor layout in two dimensions. The gantry 10 is installed in the room shown at the top of the diagram. FIG. 1 shows the dominance of the gantry size on the overall layout of an extant proton therapy facility. The approximate weight of the convention proton gantry shown in FIG. 1 is approximately 120 tons. It is even more evident if one looks at all 3 dimensions and takes into account that the diameter of the gantries exceed 13 meters. Conventional isocentric gantries are generally greater than 13 meters in diameter and up to 15 meters long.

Another feature that drives the size of extant gantries is the need to have a very long nozzle, typically over 3 meters in length, that allows for an advanced scanning technique called spot beam scanning, also known as pencil beam scanning, with minimization of the entry dose at the skin. (A nozzle of at least 2.3 meters is required even if scanning is not performed.) The spot beam scanning technique spreads a small diameter incident proton beam over the target area at a certain depth inside the patient. Electromagnets mounted in a nozzle sweep the beam in two dimensions, X-Y, over the target area. In addition the beam intensity for each 3 dimensional spot (voxel) of the target area is varied to achieve a dose distribution that conforms exactly to the target area at a precise depth. Repeating this process for a range of decreasing energies (energy stacking) allows treatment at different depth and hence of the full tumor volume with any arbitrary shape. In one extant system beam scanning is performed in one direction upstream of the last 90 degree bending magnet of the gantry. While beam scanning upstream of the last gantry dipole did effectively reduce the treatment nozzle it also resulted in a very large, heavy gantry and included a costly 90 degree bend magnet weighing about 90 tons.

Conventional gantries now on the market capable of doing advanced beam scanning techniques such as spot scanning cost in the range of $10 million to $15 million installed and are mostly over 40 feet in diameter.

Superconducting technology has been proposed for ion therapy applications before, especially for carbon ion therapy. However, at that time it was concluded that complexity of the cryogenic system and difficulty of ramping the superconducting magnets would make the application of low temperature high field magnets technically overly challenging. Selecting conventional room temperature magnets for the carbon ion gantry design at Heidelberg facility resulted in a gigantic 630 tons structure that is 16 meters in height.

An unconventional design was developed at the Paul Scherrer Institute, where the X-Y beam scanning is performed in one direction upstream of the last 90 degree bending magnet of the gantry. However, the Paul Scherrer Institute design is not isocentric around the patient and consequently it also was necessary to rotate the patient in a concentric circle that at times left the patient over 2 meters above the ground. Nevertheless, beam scanning upstream of the last gantry dipole did effectively reduce the gantry diameter from 12 meters to about 5 meters for a gantry based on conventional room temperature dipoles. Unfortunately, this also resulted in a very large, heavy (about 90 tons), and costly 90 degree bend magnet.

A superconducting gantry design recently has been proposed for particle therapy facilities. The gantry design is based on Fixed Field Alternating Gradient (FFAG) magnets, which reduce the total weight of the gantry. However, such a gantry remains very large. The gantry measures about 20 meters in length, from the rotation point to the isocenter, and has a height of about 3.2 meters. Additionally, the gantry requires a significant increase in the number of magnetic elements in the gantry system.

Thus, there is a need in the art for development of new concepts that will greatly reduce the size and associated costs of the dose delivery gantry. It is an object of the present invention to reduce the installed cost of the gantry to about 33% of that of the current offerings, the size by about 50% and the weight by a factor of ten.

SUMMARY OF THE INVENTION

In one embodiment, an isocentric gantry is configured to deliver particle radiation therapy to a patient, the gantry comprising a plurality of dipole and quadrupole electromagnets arranged in a particle beam line and configured to change a direction of the particle beam line, the plurality of dipole and quadrupole electromagnets comprising at least one superconducting magnet, and a support frame sized and configured to support the plurality of dipole and quadrupole electromagnets.

In some embodiments, the at least one superconducting magnet has variable magnetic strength. In another embodiment, the at least one superconducting magnet is rampable and the isocentric gantry has a momentum acceptance ranging from approximately +/−2% and +/−10%.

In one embodiment, the isocentric gantry further comprises at least one double bend achromat arranged in the particle beam line and configured to provide achromatic beam optics of the particle beam line. In some embodiments, the at least one double bend achromat comprises at least one dipole and at least one quadrupole.

In some embodiments, the plurality of dipole and quadrupole electromagnets comprise at least one ambient temperature magnet. In one embodiment, the at least one ambient temperature magnet comprises an ambient temperature quadrupole magnet.

In one embodiment, the isocentric gantry further comprises at least one double bend achromat and at least one ambient temperature magnet arranged in the particle beam line.

In some embodiments, the at least one superconducting magnet comprises a low temperature superconducting material. Alternatively, in another embodiment the at least one superconducting magnet comprises a high temperature superconducting material.

In one embodiment, the plurality of dipole and quadrupole electromagnets are configured to transmit the particle beam line whose energy is rapidly changed without changing a magnetic field strength or dipole settings.

In another embodiment, the isocentric gantry further comprises a scanning magnet arranged in the particle beam line configured to facilitate beam scanning.

In one embodiment, the frame is configured to rotate around an isocenter. In some embodiments, the frame has a swept volume of less than 350 cubic meters. In other embodiments, the frame has a swept volume of less than 300 cubic meters. In some embodiments, the frame has a source to isocenter distance greater than 2.2 meters. In another embodiment, the gantry is configured to focus the particle beam line at an isocenter ranging from 1 to 10 millimeters root mean squared spot size.

In some embodiments, the plurality of dipole and quadrupole electromagnets further comprise a first double bend achromat arranged as dipole-quadrupole-quadrupole-quadrupole-dipole having an approximately 60 degree bend, and a second double bend achromat arranged as dipole-quadrupole-quadrupole-quadrupole-dipole having an approximately 150 degree bend.

In another embodiment, the plurality of dipole and quadrupole electromagnets further comprise a first double bend achromat arranged as dipole-quadrupole-quadrupole-quadrupole-dipole having an approximately 60 degree bend, a second double bend achromat arranged as dipole-quadrupole-quadrupole-quadrupole-dipole having an approximately 60 degree bend, and a third double bend achromat arranged as dipole-quadrupole-quadrupole-quadrupole-dipole having an approximately 90 degree bend.

In yet another embodiment, the plurality of dipole and quadrupole electromagnets further comprise at least one double bend achromat configured to change the direction of the particle beam line by an angle between approximately 45 degrees and 90 degrees.

Methods of using an isocentric gantry to provide particle radiation therapy to patients are also provided. In one embodiment, the method comprises delivering particle beam radiation to a patient when an isocentric gantry is arranged in a first position. The isocentric gantry can comprise a plurality of dipole and quadrupole electromagnets arranged in a particle beam line and configured to change a direction of the particle beam line, the plurality of dipole and quadrupole electromagnets comprising at least one superconducting magnet, and a support frame sized and configured to support the plurality of dipole and quadrupole electromagnets. In some embodiments, the isocentric gantry comprises a plurality of dual bend achromats.

Next, the method can comprise rotating the support frame of the isocentric gantry to arrange the isocentric gantry in a second position. The support frame of the isocentric gantry can be configured to rotate up to 360 degrees. In some embodiments, the method comprises rotating the support frame of an isocentric gantry having a swept volume of less than 300 cubic meters to arrange the isocentric gantry in a second position.

The method can further comprise delivering particle beam radiation to a patient when the isocentric gantry is arranged in the second position.

BRIEF DESCRIPTION OF THE DRAWINGS

FIGS. 8a-8b are side and end views of a compact gantry assembly of the compact gantry of FIGS. 5 and 6a.

DETAILED DESCRIPTION

Through use of the superconducting magnet technology for beam delivery systems, it is proposed to reduce the capital cost of proton systems to be competitive with that of advanced x-ray systems on a per treatment fraction use basis. The compact isocentric gantry design for particle therapy presented herein is based upon innovative superconducting magnet systems.

Isocentric gantry systems described herein can include a number of superconducting magnets to reduce the overall size and swept volume of the gantry assembly. The coil windings of a superconducting magnet are typically made of wires or tapes of superconducting material. During operation, the magnet coils must be cooled below their critical temperature; the temperature at which the superconducting material changes from the normal resistive state and becomes a superconductor. Cryocoolers can be used to reach the temperature of about 5 degrees Kelvin required for most common superconducting material. There are two options for a fast ramp superconducting sector magnet: fully saturated iron with low temperature superconductors (LTS) conductors, or high temperature superconductors (HTS) conductors at low or elevated temperatures. NbTi, an LTS conductor, allows the broadest range of dipole magnet engineering solutions but has the narrowest range of operating temperatures. HTS operation at elevated temperatures would allow use of cryocoolers with more cooling power without increases in electrical power.

One novel aspect of the gantry design is the use of achromatic superconducting multi-function magnet systems. An achromat refers to an arrangement of the magnets of the gantry so the beam optics of the system is achromatic.

Figure 1:
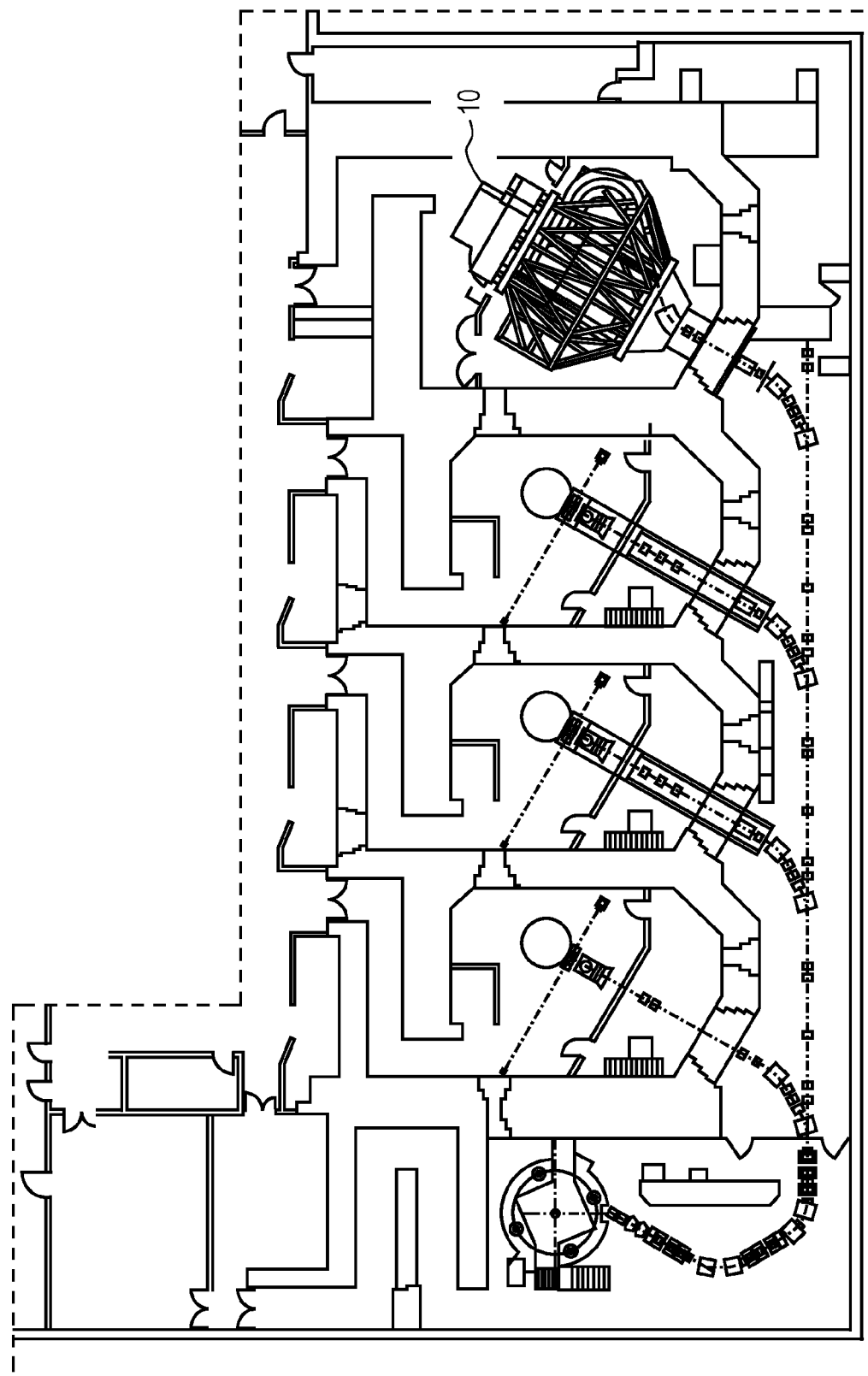
FIG. 1 is a treatment room floor layout of a conventional proton therapy center.
Figure 2A:
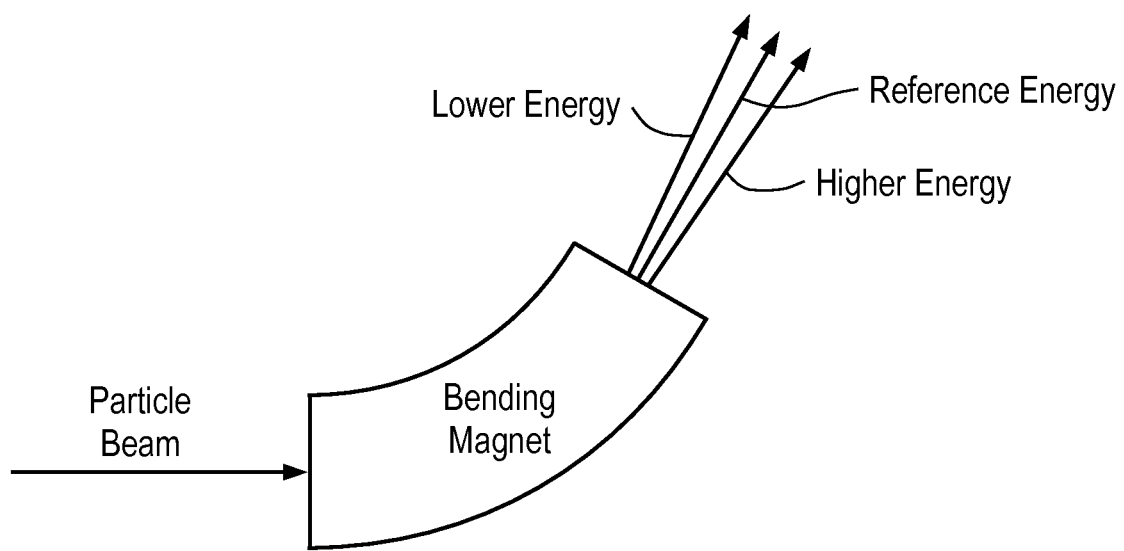
FIG. 2a shows aberrations in beam transport through the magnets of the gantry.

Achromatic systems are designed to compensate for the divergence resulting from the finite energy spread in the beam which is always present in practical ion beams used in particle therapy. Modern spot beam scanning techniques require precise beam transport for accurate and reproducible dose delivery to the patient. However, when charged particles with slightly different energy traverse the same magnetic field, they experience different deflections. FIG. 2a shows aberrations in beam transport through the magnets of the gantry. When particles with different energies travel on different trajectories they have different focal positions. In such a case, different parts of the beam spot may have different penetration ranges in the patient body, which would lead to loss of dose delivery precision—a main advantage of charged particle beams. This effect is similar to chromatic aberrations in optical systems. Achromatic properties of the gantry beam transport system eliminate correlation between the beam energy and beam position and angle at the isocenter. Such optical properties of the magnet gantry system can be generated using double bend achromats (DBA), making beam transport through the gantry magnets more robust and insensitive to small energy variations of the incoming beam. (M. Pavlovic, L. Cincura, E. Griesmayer and T. Schreiner, "A study of dispersion effects in transport of ion-therapy beams" Journal of Electr. Eng. 58(1), 33-38 (2007)).

Figure 2B:
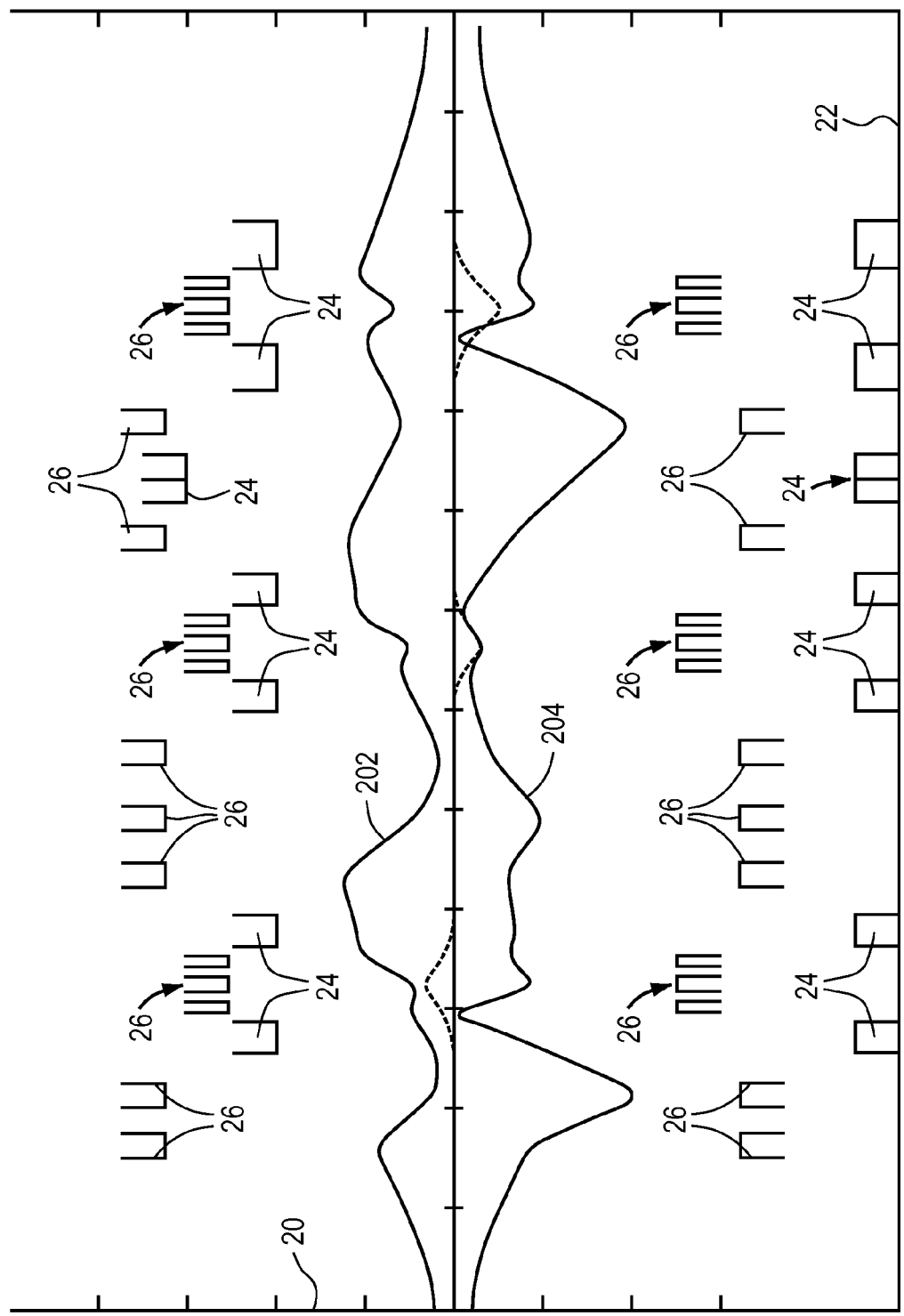
FIG. 2b shows the beam envelopes through gantry designed using the 60-deg and 90-deg double bend achromats.

FIG. 2b shows the beam transport envelopes (beam size) in horizontal and vertical planes for beams passing through an isocentric gantry based upon two DBA magnet systems. The vertical axis 20 represents beam size while the horizontal axis 22 represents the position along the gantry. Boxes 24 represent the position and aperture of dipole magnets while boxes 26 represent the position and aperture for quadrupole magnets. The trace 202 indicate horizontal beam size along the beam path with 0.1% momentum spread, while the trace 204 is calculated for ±3% momentum spread. This demonstrates the large momentum acceptance that can be achieved through the use of a DBA magnet system in an isocentric gantry.

Figure 3:
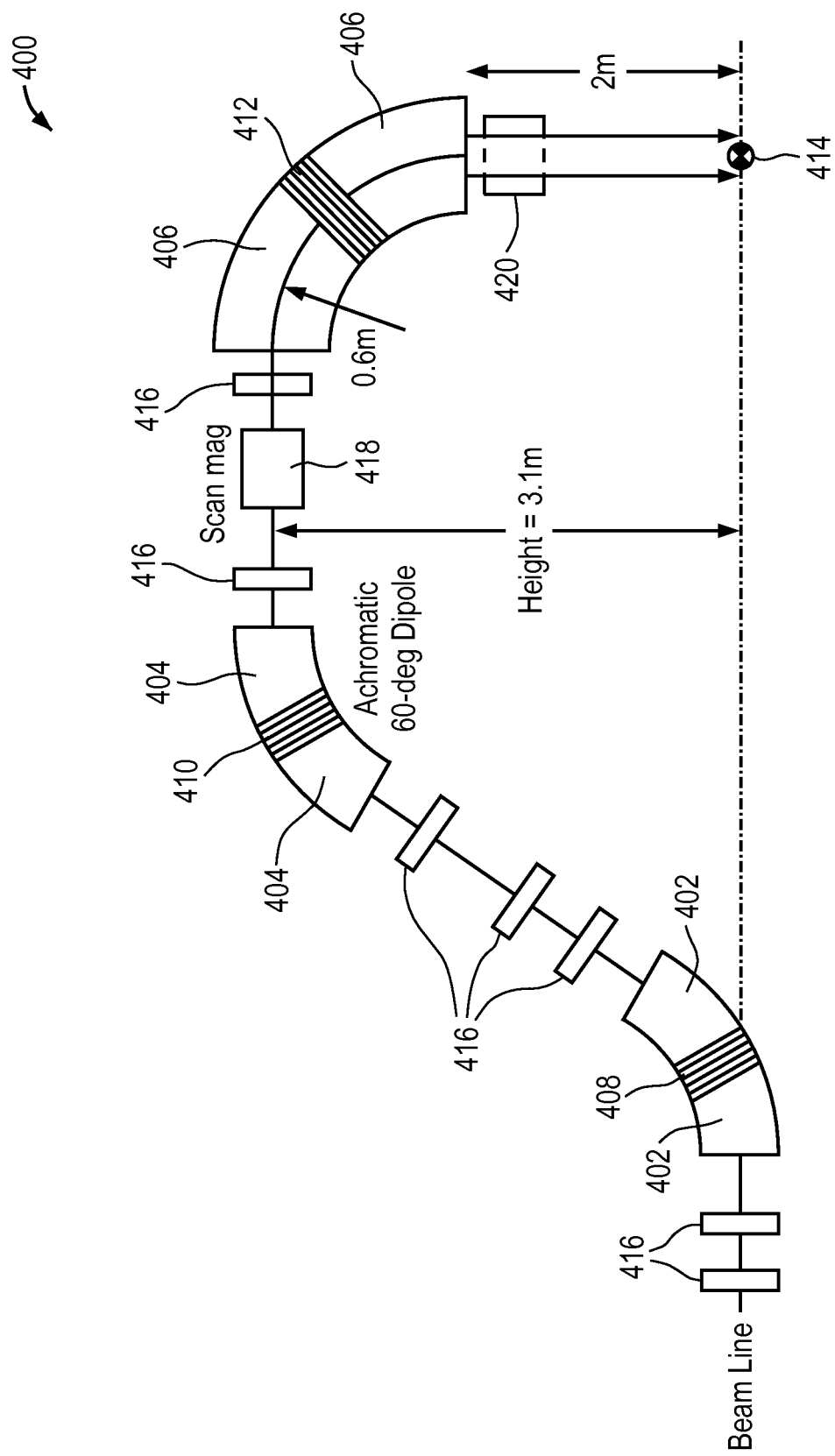
FIG. 3 is a side view of the arrangement of the beam line components in one embodiment of a compact gantry.
Figure 4:
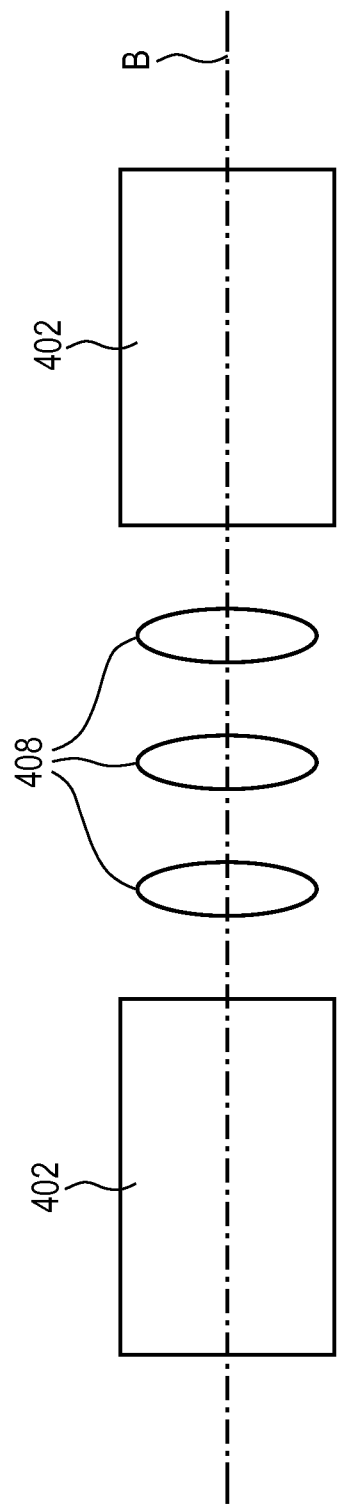
FIG. 4 is a schematic view of an arrangement of components in a portion of a compact gantry.

Various magnet system angle combinations are possible as shown in the figures. FIGS. 3-4 illustrate that each system used in the gantries can have one or more horizontally focusing quadrupole magnets in the middle to make each system doubly achromatic. For example, in FIG. 3, dipole 402 can have superconducting quadrupole magnets 408, dipole 404 can have superconducting quadrupole magnets 410, and dipole 406 can have superconducting quadrupole magnets 412 positioned in the middle of each dipole. FIG. 4 shows an exploded, close up view of dipole 402, superconducting quadrupole magnets 408, and beam line B.

The isocentric gantries described herein can be configured to change the direction of a particle beam line by 90 degrees (e.g., change the direction of a horizontal beam line to a vertical beam line) or any other angle required incident on the patient. In some embodiments, the gantry comprises a frame and utilizes three DBA magnet systems in the frame to change the direction of the particle beam. FIG. 4 illustrates one embodiment of a DBA magnet system comprising a dipole-quadrupole-quadrupole-quadruple-dipole (DQQQD) magnet system, which include dipoles 402 on both sides of three superconducting quadrupoles 408.

In one embodiment a gantry comprises two 60 degree DBA magnet systems and one achromatic 90 degree DBA magnet system. By way of example, one design of a magnet system angle combination for a compact gantry is illustrated in FIG. 3. The gantry 400 can use the superconducting DBA electromagnet systems or dipoles 402, 404, and 406. As shown in FIG. 3, dipoles 402 and 404 can be achromatic 60 degree dipoles, and dipole 406 can be an achromatic 90 degree dipole, which results in bending a horizontal beam line into a vertical beam line for delivery to an isocenter 414. Additionally, each dipole set 402, 404, and 406 can include superconducting quadruple magnets 408, 410, and 412 positioned in the middle of each dipole set, respectively, to reduce the overall size and swept volume of the gantry. In some embodiments, the bending radius of the 90 degree dipole can be about 60 centimeters, with about 2.0 meter distance reserved from the exit of the last gantry dipole 406 to the isocenter 414, resulting in a diameter of such an orthogonal gantry of approximately 7 meters.

In addition to using superconducting quadrupole magnets in the middle of each bend system, in some embodiments, room temperature quadrupole magnets 416 can be placed in the beam line between dipoles for use in transmitting beams with rapidly changing energies. Referring to FIG. 3, room temperature quadrupole magnets 416 can be used in the beam line before dipole 402, in between dipoles 402 and 404, and in between dipoles 404 and 406. Also shown in FIG. 3 is a scan magnet 418 in place before the last dipole 406, or in an alternative embodiment, can be placed after the dipole 406 as represented by dotted box 420. When the scanning magnet is in position 420, the distance from the dipole 406 to the isocenter 404 is reduced.

Figure 5:
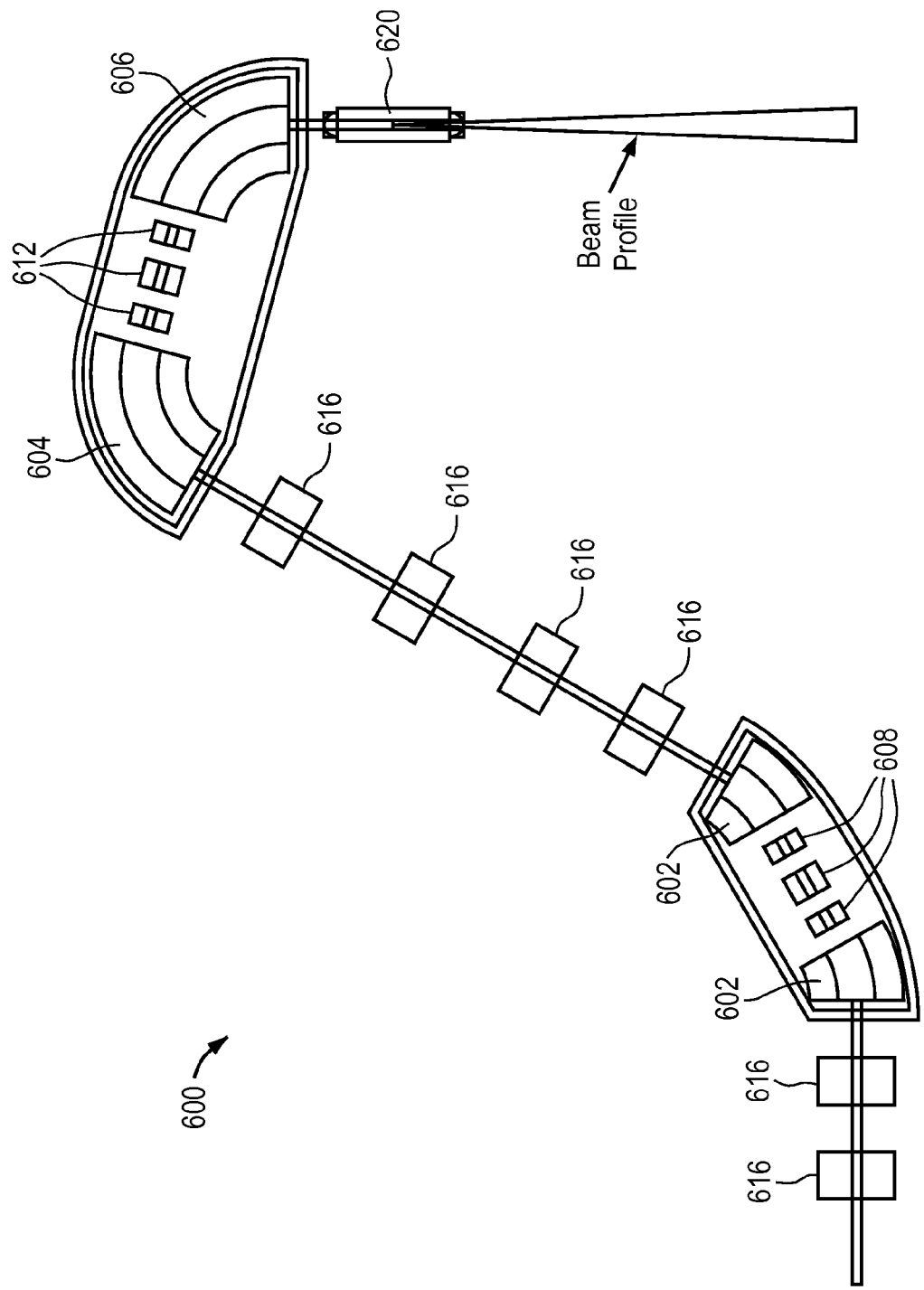
FIG. 5 is side view of the arrangement of the beam line components in another embodiment of a compact gantry.

FIG. 5 shows another embodiment of a gantry 600, similar to the design shown in FIG. 3. However, in FIG. 5 the size of the compact gantry is adjusted by utilizing different dipole angles and includes only two DBA electromagnet sets (e.g., a 60 degree DQQQD set and a 150 degree DQQQD set) instead of the three DBA sets in the embodiment of FIG. 3 (e.g., two 60 degree DQQQD sets and a 90 degree DQQQD set). In the embodiment shown in FIG. 5, dipoles 602 and superconducting quadrupoles 608 form a 60 degree bend, and dipoles 604 and 606 and superconducting quadrupoles 612 combine to form a 150 degree bend. In the embodiment of FIG. 5, superconducting quadrupoles 608 can be disposed between dipoles 602, and superconducting quadrupoles 612 can be disposed between dipoles 604 and 606. When dipole 604 bends at an angle higher than 60 degrees (e.g., when dipole 604 is 70 degrees and dipole 606 is 80 degrees, or dipoles 604 and 606 are both 75 degrees), the gantry can assume a shorter horizontal width. Thus, the gantry 600 of FIG. 5 will be narrower in length than the gantry 400 of FIG. 3 (which utilizes a 60 degree bend), however gantry 600 will have a larger overall height than gantry 400.

It should be understood that many combinations of angles can be used to design the beam transport that best optimizes the size and cost of the gantry. Various compact gantry envelopes are envisioned that may adjust diameter, overall height, length, and other dimensions as a result of beam line component selection and combinations as described herein.

It is important to note that FIG. 5 illustrates a side view of the magnet components for a case where additional room temperature magnets are used to make it possible to accommodate fast energy changes before the gantry. In addition to using superconducting quadrupole magnets 608 and 612 in the middle of each DBA electromagnet set, in some embodiments, room temperature quadrupole magnets 616 can be placed in the beam line between the DBA electromagnet systems. The gantry system can also optionally include multiaxis scanning magnet 620 to facilitate beam scanning, as described above.

Figure 6A:
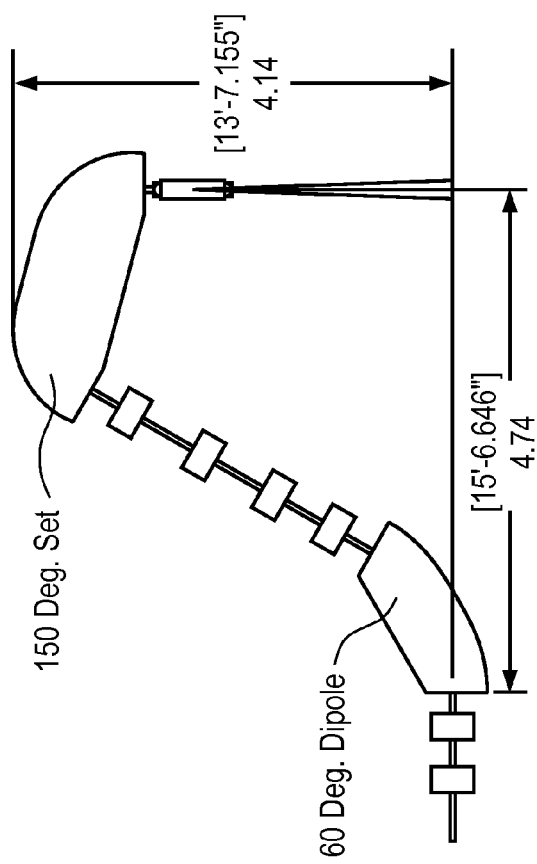
FIG. 6a includes end, side and isometric views of a compact gantry.
Figure 6B:
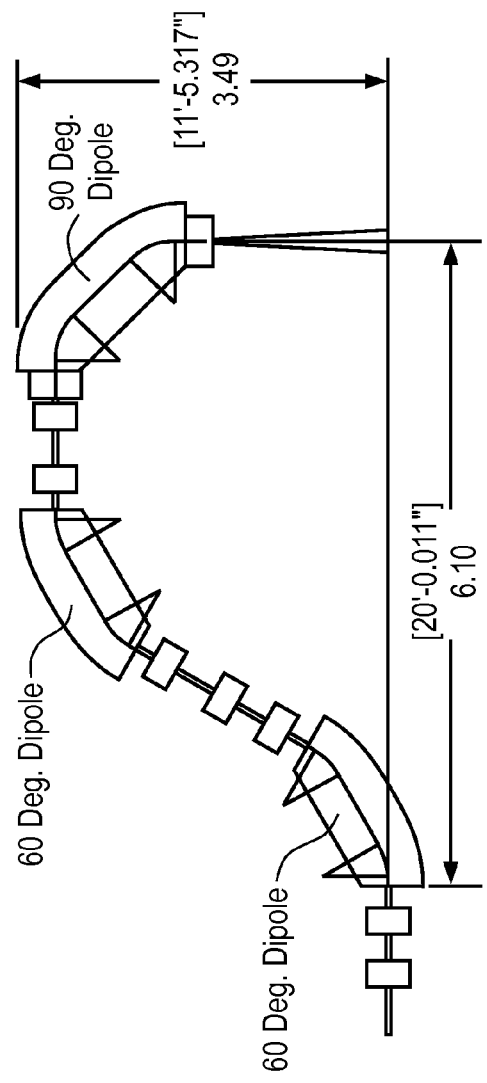
FIG. 6b includes end, side and isometric views of another compact gantry embodiment.

FIGS. 6a-6b further illustrate how the overall size and volume of a compact gantry changes when the angles of each dipole are adjusted. The volume of the gantry can be assessed by referring to the swept volume. The swept volume is measured by multiplying pi times the length from the rotating base to the isocenter by the radius of the gantry squared. In one embodiment, the swept volume of a frame of the gantry would be less than 300 cubic meters. FIG. 6a provides end, side and isometric views respectively of the beam line components of the embodiment of FIG. 5. FIG. 6a can represent the gantry described above in FIG. 5, having a 60 degree dipole followed by a 150 degree set (e.g., 60 degrees and 90 degrees dipoles, 70 degrees and 80 degrees dipoles, two 75 degrees dipoles, etc). As can be seen from the side view in FIG. 6a, the resulting gantry dimensions can have a length of 4.74 m and a radius of 4.14 m, resulting in a total swept volume of 255.1 cubic meters [(3.14*(4.14)^2*4.74)].

Figure 7B:
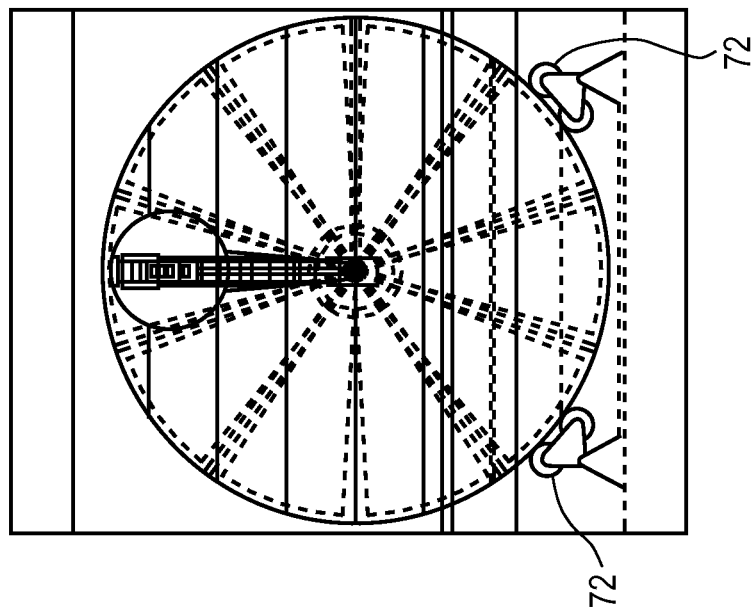
FIGS. 7a-7b are side and end views of a compact gantry assembly of the compact gantry of FIG. 6b.
Figure 7A:
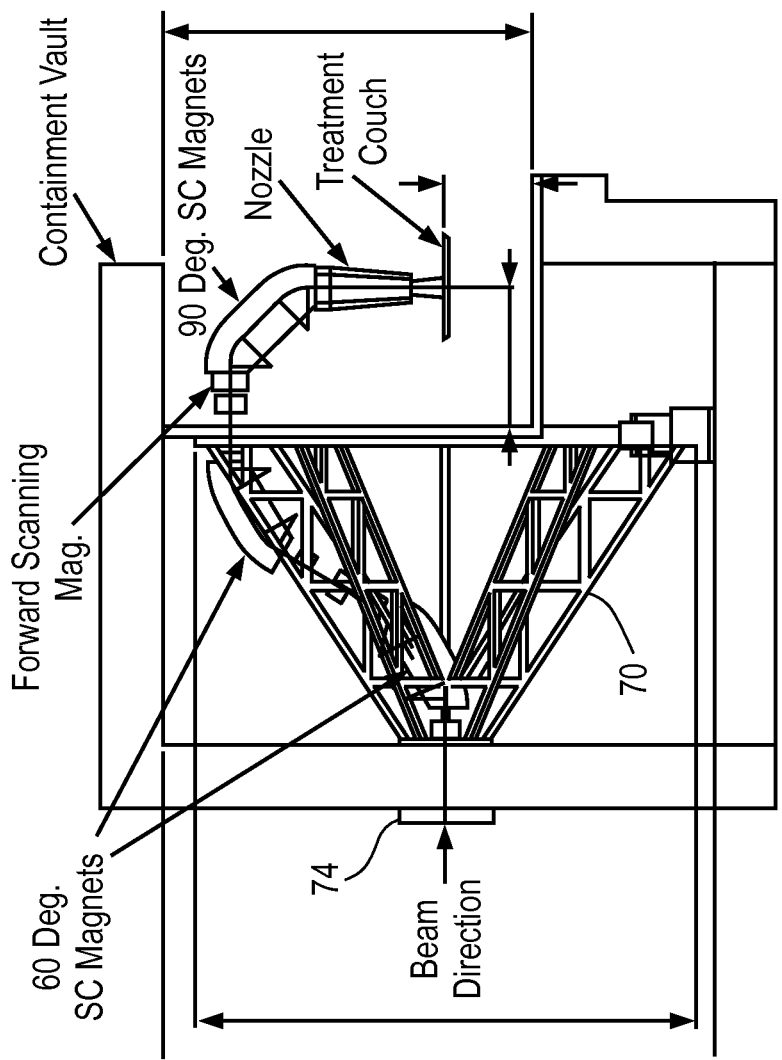

FIG. 6b provides end, side and isometric views respectively of the beam line components of the embodiment of FIGS. 3 and 7a, 7b. FIG. 6b can represent the gantry described above in FIG. 3, having a 60 degree dipole followed by a 60 degree dipole and then a 90 degrees dipole. As can be seen from the side view in FIG. 6b, the resulting gantry can have a length of 6.1 m and a radius of 3.49 m, resulting in a total swept volume of 291.3 cubic meters [(3.14*(3.49)^2*6.1)]. Thus, by adjusting the relative angles of each of the dipoles used in the gantry, the total size and volume of the gantry can be adjusted, depending on the application and space available at the center in which the gantry is to be used.

FIGS. 7a-7b illustrate side and end views, respectively, of one embodiment of a gantry assembly, which can be the compact gantry described above in FIG. 3 and FIG. 6b, including representative support structure or frame 70 needed when it is installed for use in a proton therapy center. FIGS. 7a-7b also illustrate an embodiment of a gantry assembly wherein the gantry can be mounted to a rotating superstructure, which can rotate radially around on two bearings 72. A rear bearing 74 can be positioned at or near the first dipole and rotates about the beam line. In FIG. 7a, the portion of the gantry assembly to the right of the rear bearing 74 may be the only portion of the gantry that is visible from a treatment room. The rest of the gantry assembly (e.g., the portion to the left of the rear bearing) may be behind a wall and out of site from the patient. Depending on the type of therapy to be delivered to the patient, the entire gantry assembly can rotate using the front and rear bearings to adjust the angle of the proton beam to be delivered to the patient. FIG. 7b is an end view of the gantry illustrating how the gantry can rotate the nozzle around an isocenter using bearings 72.

Figure 8B:
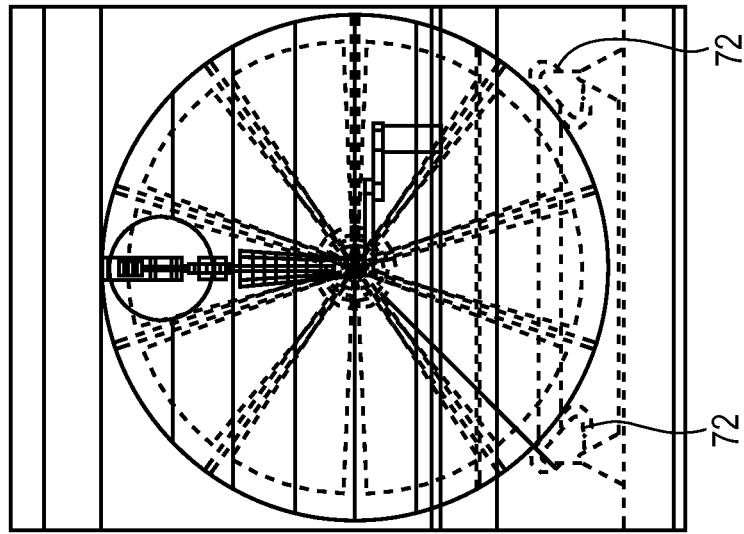
Figure 8A:
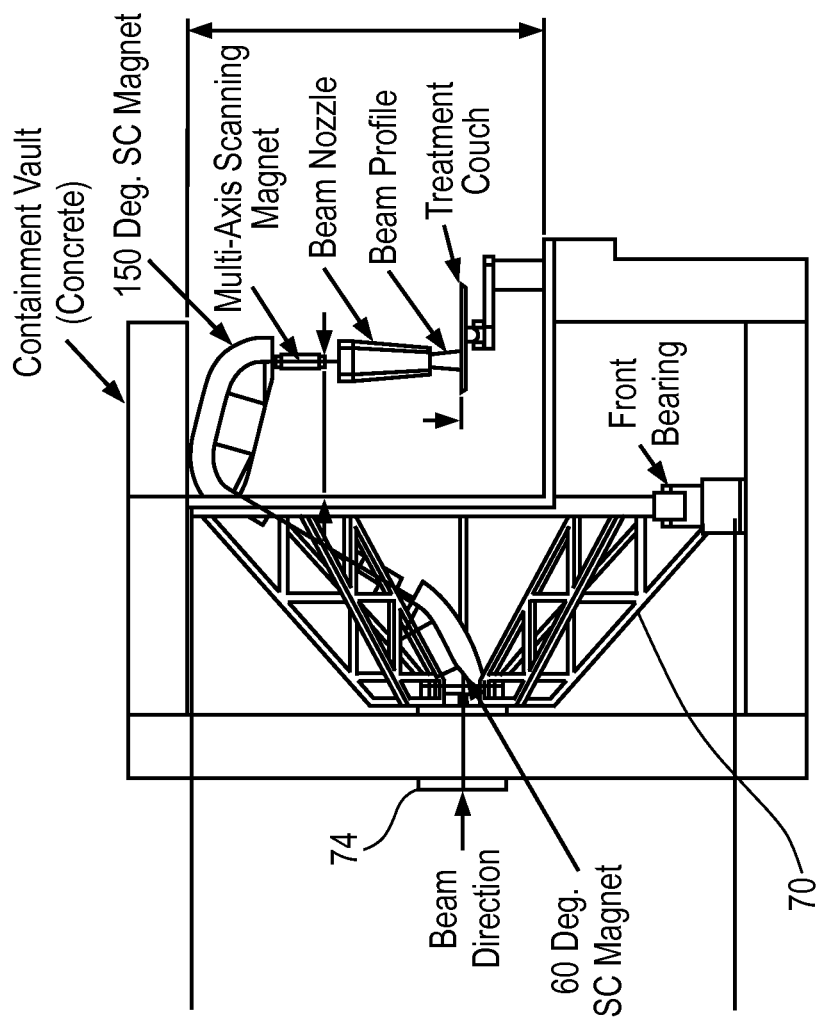

FIGS. 8a-8b illustrate side and end views, respectively, of another embodiment of a gantry assembly (which can be the compact gantry described FIG. 5 and FIG. 6a). Comparing FIGS. 7a-7b with FIGS. 8a-8b, it can be seen how adjusting the angles of the dipoles affects the size of each gantry assembly. For example, the assembly of FIGS. 7a-7b has a total height measured from the bottom of the front bearing to the top of the upper dipole of 26'-2.961". The assembly of FIGS. 8a-8b has a total height of 27'-2.77". However, the assembly of FIGS. 7a-7b has a total width (from rear bearing to isocenter) of 22'-11.591", while the assembly of FIGS. 8a-8b has a total width of 18'-4.47".

Figure 9:
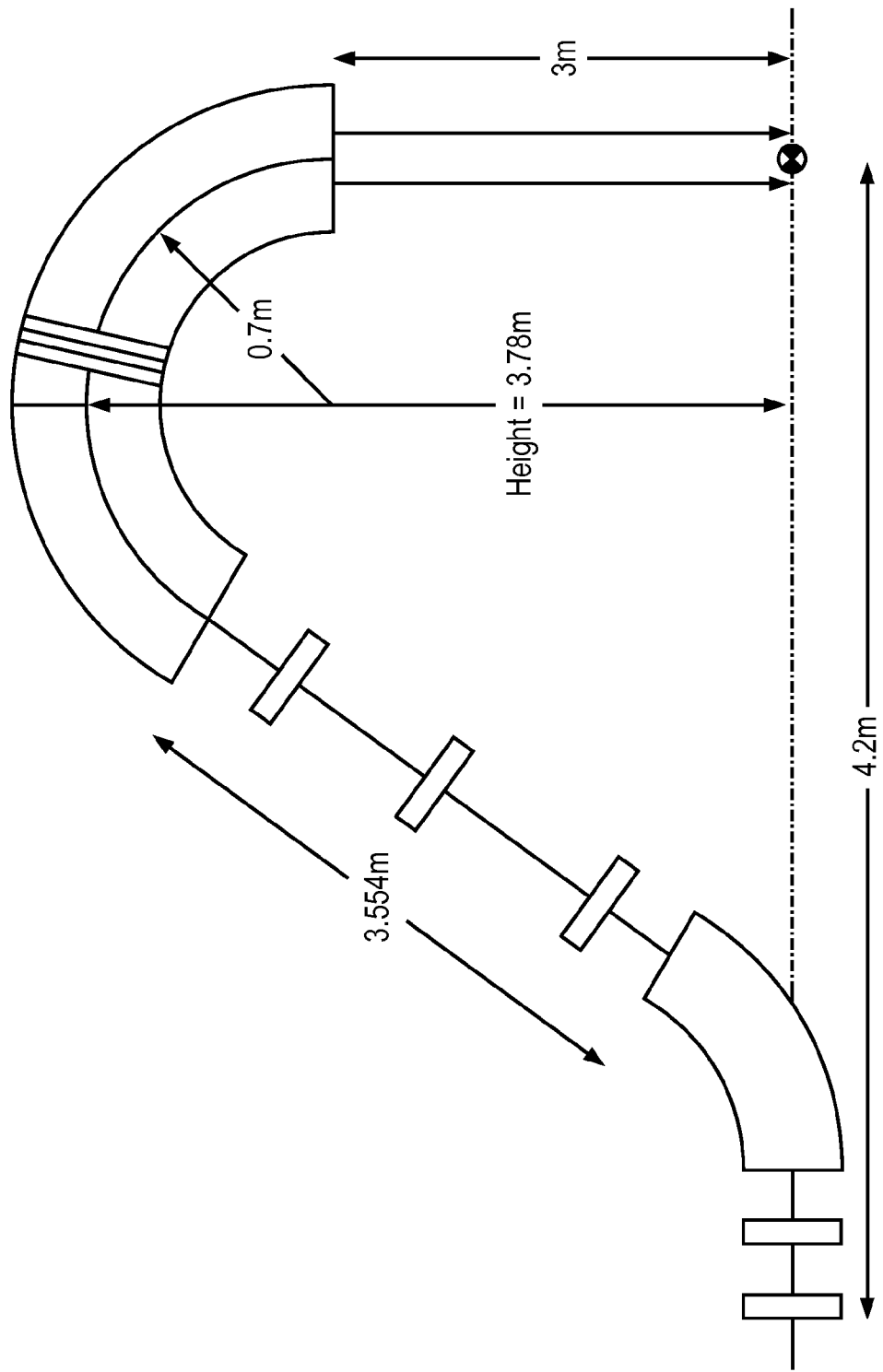
FIG. 9 is side view of the arrangement of the beam line components in another embodiment of a compact gantry.

FIG. 9 is a side view of the arrangement of the beam line components in one embodiment of a compact gantry, wherein superconducting magnets enable the bending of a horizontal beam line into a vertical beam line for delivery to an isocenter at the treatment site. With about 3.0 meter distance reserved from the exit of the last gantry, the diameter of such an orthogonal gantry would be about 7 meter. The gantry can also be made as short as 6 meter reducing the total volume needed for the gantry installation by additional factor of ten less than the current art.

The magnet system can be comprised of dipole and quadrupole electromagnets having variable magnetic strength. The magnetic strength of the electromagnet system can continuously change or be ramped. Rampable magnets based on superconducting material are suitable for a compact gantry design that can best meet the clinical demands of particle radiation therapy. Optimization of the gantry parameters provides that the dipoles can ramp from about 2 Tesla to 4.0 Tesla in 30 seconds or less.

Where it is difficult to achieve a sufficient fast ramp with the superconducting magnets, some room temperature quadrupoles can be included in the design for small beam optics modifications. The replacement of some ambient or room temperature magnets with superconducting dipole and quadrupole magnets can result in a much smaller and lighter gantry. One can also consider reducing the number of quadrupole magnets in the gantry design optimization which would result in cost savings. For instance, the magnet system could comprise arrangements of dipole and quadrupoles such as a dipole-quadrupole-quadruple-dipole (DQQD) magnet system, and dipole-quadruple-dipole (DQD). Conversely, more quadrupoles could be utilized such as dipole-quadrupole-quadrupole-quadruple-dipole (DQQQQD), however adding more quadrupoles adds more weight and expense to the gantry. It is important to note that by changing the number of quadrupole magnets in the gantry design the optics of the magnetic field system would have to be redesigned.

In some embodiments the magnets can be made from low temperature superconductors, and in other manifestations the magnets can be made from high temperature superconductors.

In some embodiments, the rotation of the gantry can rotate +/−180 or +/−90 degrees from the treatment room floor. The main benefit of the gantry is to allow geometrical flexibility of beam treatment angles with respect to a patient, who is usually lying on the treatment table.

In other embodiments, the gantry can have a diameter of 9 meters or less. This provides a gantry with a diameter of about 66% of the typical gantries commercially available today. Conventional isocentric gantries are generally greater than 13 meters in diameter and up to 15 meters long. Even modest reduction of the gantry diameter to 9 meters without changing its length reduces the gantry volume by a factor of two, which makes significant saving in the cost of the building and concrete required for radiation shielding.

Some embodiments of a gantry nozzle may include a compact, combined function scanning magnet and control systems to produce the desired beam distributions. Beam scanning upstream of the last gantry dipole can significantly reduce size of the nozzle, and has been used in conventional systems to reduce the gantry diameter. However, when this has been done in the conventional systems the last gantry dipole typically generated large dispersion inside the gantry beam line. The consequence is that it limits its momentum acceptance ($\Delta p/p$) to about 1% substantially. It is also difficult with such systems to reduce the beam spot below 5 millimeter radius at the isocenter without further sacrificing momentum acceptance and need to increase the aperture of the last dipole. The present gantry design has been able to resolve this issue and is able to reduce size without beam scanning before or upstream of the last dipole.

In one embodiment, the superconducting magnets which comprise a magnetic beam transport system can have a momentum acceptance between ±2% to ±6%. The dispersion function in the superconducting DBA could be about 42 centimeters, which for a typical 2 inch beam pipe would correspond to 6% momentum acceptance. For instance, the momentum acceptance in the achromatic dipole with a 60-degree bend will be about 6%, which corresponds to +/−20 MeV energy acceptance at 200 MeV. This increased momentum acceptance of the DBA system alleviates ramp rate requirements for the superconducting magnets. Therefore, a proton beam transmission from 180 MeV to 220 MeV can be achieved with such dipole without changing the magnet setting. Or stated differently, such DBA system can transmit a beam whose energy is rapidly changed to irradiate different layers of the tumor volume in order to achieve desired dose distribution in depth without changing the magnet settings. This is a significant advantage for proton therapy. The designs described herein enable fast energy changes before the gantry (i.e., before the beam reaches the rear bearing or the first gantry mounted dipole).

In another embodiment, the gantry design is compatible with advanced beam scanning techniques. The gantry design provides ease of operation, allows maximum flexibility for treatment plans including Intensity Modulated Proton Therapy (IMPT) using spot beam scanning capability, easy access to patients on the treatment table while being both as light and compact as possible. The gantry further enables advanced beam scanning capability while remaining isocentric. For instance, the beam optics of the system will be able to focus the beam at the isocenter to a range from 1 millimeter (mm) to 10 millimeters root mean square (rms) spot size.

In some embodiments, treatment field sizes can be 20×30 centimeters.

Still other embodiments may include a computer controlled digital range modulator utilizing the energy stacking process, and a redundant multi-plane ion chamber detector system (the Patient Dose Monitor) to measure proton dose, position, symmetry and uniformity during treatment.

In some embodiments, the source to isocenter distance (SAD) is more than 2.2 meters. Short SAD results in elevated skin (entrance) dose to the patient. Consideration must be given for the fact that any increase in SAD will add that to the radius of the gantry. Therefore there is a trade-off between any increase in the SAD and the containment of the size of the gantry.

Another advantage is that the achromatic properties of the gantry magnet systems will also improve the percentage of the beam transmitted from the energy degrader to the patient. The current gantries used in the majority of proton therapy systems transmit approximately 1% to 3% of the beam from the accelerator to the patient depending on the final energy required. Some embodiments of the gantry described herein provide transmission from the energy degrader to the patient increasing to about 10% and to even as much as 20%. The result is a decrease in the beam loss by a factor of 5 to 7 and therefore a significant reduction in the amount of concrete shielding needed around the accelerator and beam transport system. Another benefit of this increased transmission is a lowered demand from the accelerator.

Additionally, the use of superconducting magnet systems reduce the requirements for overall electrical power and for power supplies.

The advantages of utilizing superconducting magnets in an isocentric gantry are significant, including: reduced overall clinical space, power supplies, total mass and required electrical power. Since superconducting magnets do not suffer thermal degradation, they can be designed with tighter margins without increasing risk or reducing robustness, which further lowers overall cost. In embodiments where high temperature conductors are utilized at elevated temperatures, then additional economies can be realized.

By using superconducting magnets and achromatic optics, the size of the gantry can be reduced. The ability to reduce the beam delivery gantry diameter to about 7 meters the length reduced to about 8 meters showcases a principle advantage of the invention. Consequently the volume occupied by the gantry would be reduced by up to a factor of ten as compared to systems commercially available today. Reduction in volume would result in reduction of the weight by a similar amount. The advent of smaller scale, lower cost proton therapy systems will allow proton therapy to play a much greater role in radiation therapy and bring this advanced form of therapy to many more patients who will benefit greatly from its use.

Methods of using an isocentric gantry to provide particle radiation therapy to patients are also provided. In one embodiment, the method comprises delivering particle beam radiation to a patient when an isocentric gantry is arranged in a first position. The isocentric gantry can comprise a plurality of dipole and quadrupole electromagnets arranged in a particle beam line and configured to change a direction of the particle beam line, the plurality of dipole and quadrupole electromagnets comprising at least one superconducting magnet, and a support frame sized and configured to support the plurality of dipole and quadrupole electromagnets. In some embodiments, the isocentric gantry comprises a plurality of dual bend achromats and is configured to change the direction of the particle beam line by approximately 45 to 90 degrees.

Next, the method can comprise rotating the support frame of the isocentric gantry to arrange the isocentric gantry in a second position. The support frame of the isocentric gantry can be configured to rotate up to 360 degrees. In some embodiments, the method comprises rotating the support frame of an isocentric gantry having a swept volume of less than 300 cubic meters to arrange the isocentric gantry in a second position.

The method can further comprise delivering particle beam radiation to a patient when the isocentric gantry is arranged in the second position.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An isocentric gantry configured to deliver particle radiation therapy to a patient, comprising:
   a plurality of dipole and quadrupole electromagnets arranged in a particle beam line and configured to change a direction of the particle beam line, the plurality of dipole and quadrupole electromagnets comprising at least one superconducting magnet and at least one ambient temperature magnet, wherein the isocentric gantry has a momentum acceptance ranging from approximately +/−2% and +/−10% without changing a setting of the plurality of dipole and quadrupole electromagnets; and
   a support frame sized and configured to support the plurality of dipole and quadrupole electromagnets.

2. The isocentric gantry of claim 1, wherein the at least one superconducting magnet has variable magnetic strength.

3. The isocentric gantry of claim 1, further comprising at least one double bend achromat arranged in the particle beam line and configured to provide achromatic beam optics of the particle beam line.

4. The isocentric gantry of claim 3, wherein the at least one double bend achromat comprises at least one dipole and at least one quadrupole.

5. The isocentric gantry of claim 1, wherein the at least one superconducting magnet is rampable.

6. The isocentric gantry of claim 1, further comprising at least one double bend achromat and at least one ambient temperature magnet arranged in the particle beam line.

7. The isocentric gantry of claim 1, wherein the at least one superconducting magnet comprises a low temperature superconducting material.

8. The isocentric gantry of claim 1, wherein the at least one superconducting magnet comprises a high temperature superconducting material.

9. The isocentric gantry of claim 1, wherein the plurality of dipole and quadrupole electromagnets are configured to transmit the particle beam line whose energy is rapidly changed without changing a magnetic field strength or dipole settings.

10. The isocentric gantry of claim 1, further comprising a scanning magnet arranged in the particle beam line configured to facilitate beam scanning.

11. The isocentric gantry of claim 1, the frame being configured to rotate around an isocenter.

12. The isocentric gantry of claim 11, wherein the frame has a swept volume of less than 300 cubic meters.

13. The isocentric gantry of claim 12, wherein the frame has a source to isocenter distance greater than 2.2 meters.

14. The isocentric gantry of claim 1, wherein the gantry being configured to focus the particle beam line at an isocenter ranging from 1 to 10 millimeters root mean squared spot size.

15. The isocentric gantry of claim 1, wherein the at least one ambient temperature magnet comprises an ambient temperature quadrupole magnet.

16. The isocentric gantry of claim 1, wherein the plurality of dipole and quadrupole electromagnets further comprise a first double bend achromat arranged as dipole-quadrupole-quadrupole-quadrupole-dipole having an approximately 60 degree bend, and a second double bend achromat arranged as dipole-quadrupole-quadrupole-quadrupole-dipole having an approximately 150 degree bend.

17. The isocentric gantry of claim 1, wherein the plurality of dipole and quadrupole electromagnets further comprise a first double bend achromat arranged as dipole-quadrupole-quadrupole-quadrupole-dipole having an approximately 60 degree bend, a second double bend achromat arranged as dipole-quadrupole-quadrupole-quadrupole-dipole having an approximately 60 degree bend, and a third double bend achromat arranged as dipole-quadrupole-quadrupole-quadrupole-dipole having an approximately 90 degree bend.

18. The isocentric gantry of claim 1, wherein the plurality of dipole and quadrupole electromagnets further comprise at least one double bend achromat configured to change the direction of the particle beam line by an angle between approximately 45 degrees and 90 degrees.

19. An isocentric gantry configured to deliver particle radiation therapy to a patient, comprising:
   a plurality of dipole and quadrupole electromagnets arranged in a particle beam line and configured to change a direction of the particle beam line, the plurality of dipole and quadrupole electromagnets comprising at least one superconducting magnet and at least one ambient temperature magnet; and a support frame sized and configured to support the plurality of dipole and quadrupole electromagnets.

20. The isocentric gantry of claim 19, wherein the at least one ambient temperature magnet comprises an ambient temperature quadrupole magnet.

21. An isocentric gantry configured to deliver particle radiation therapy to a patient, comprising:

a plurality of dipole and quadrupole electromagnets arranged in a particle beam line and configured to change a direction of the particle beam line, the plurality of dipole and quadrupole electromagnets comprising at least one superconducting magnet, at least one double bend achromat, and at least one ambient temperature magnet; and a support frame sized and configured to support the plurality of dipole and quadrupole electromagnets.

22. An isocentric gantry configured to deliver particle radiation therapy to a patient, comprising:

a plurality of dipole and quadrupole electromagnets arranged in a particle beam line and configured to change a direction of the particle beam line, the plurality of dipole and quadrupole electromagnets comprising at least one superconducting magnet, the plurality of dipole and quadropole electromagnets being configured to transmit the particle beam line whose energy is rapidly changed without changing a magnetic field strength or dipole settings; and a support frame sized and configured to support the plurality of dipole and quadrupole electromagnets.

23. An isocentric gantry configured to deliver particle radiation therapy to a patient, comprising:

a plurality of dipole and quadrupole electromagnets arranged in a particle beam line and configured to change a direction of the particle beam line, the plurality of dipole and quadrupole electromagnets comprising at least one superconducting magnet, wherein the plurality of dipole and quadrupole electromagnets further comprise a first double bend achromat arranged as dipole-quadrupole-quadrupole-quadrupole-dipole having an approximately 60 degree bend, and a second double bend achromat arranged as dipole-quadrupole-quadrupole-quadrupole-dipole having an approximately 150 degree bend; and a support frame sized and configured to support the plurality of dipole and quadrupole electromagnets.

24. An isocentric gantry configured to deliver particle radiation therapy to a patient, comprising:

a plurality of dipole and quadrupole electromagnets arranged in a particle beam line and configured to change a direction of the particle beam line, the plurality of dipole and quadrupole electromagnets comprising at least one superconducting magnet, wherein the plurality of dipole and quadrupole electromagnets further comprise a first double bend achromat arranged as dipole-quadrupole-quadrupole-quadrupole-dipole having an approximately 60 degree bend, a second double bend achromat arranged as dipole-quadrupole-quadrupole-quadrupole-dipole having an approximately 60 degree bend, and a third double bend achromat arranged as dipole-quadrupole-quadrupole-quadrupole-dipole having an approximately 90 degree bend; and a support frame sized and configured to support the plurality of dipole and quadrupole electromagnets.

25. An isocentric gantry configured to deliver particle radiation therapy to a patient, comprising:

a plurality of dipole and quadrupole electromagnets arranged in a particle beam line and configured to change a direction of the particle beam line, the plurality of dipole and quadrupole electromagnets comprising at least one superconducting magnet, wherein the plurality of dipole and quadrupole electromagnets further comprise at least one double bend achromat configured to change the direction of the particle beam line by an angle between approximately 45 degrees and 90 degrees; and a support frame sized and configured to support the plurality of dipole and quadrupole electromagnets.

26. An isocentric gantry configured to deliver particle radiation therapy to a patient, comprising:

a plurality of dipole and quadrupole electromagnets arranged in a particle beam line and configured to change a direction of the particle beam line, the plurality of dipole and quadrupole electromagnets comprising at least one superconducting magnet, the plurality of dipole and quadrupole electromagnets being configured to focus the particle beam line at an isocenter ranging from 1 to 10 millimeters root mean squared spot size; and a support frame sized and configured to support the plurality of dipole and quadrupole electromagnets.

* * * * *